(12) United States Patent
Shi (10) Patent No.: US 10,470,775 B2
(45) Date of Patent: Nov. 12, 2019

(54) LIGATION DEVICE

(71) Applicant: Hangzhou AGS MedTech Co., Ltd., Hangzhou, Zhejiang (CN)

(72) Inventor: Baiming Shi, Zhejiang (CN)

(73) Assignee: Hangzhou AGS MedTech Co., Ltd., Hangzhou (CN)

( * ) Notice: Subject to any disclaimer, the term of this patent is extended or adjusted under 35 U.S.C. 154(b) by 302 days.

(21) Appl. No.: 15/527,707

(22) PCT Filed: Oct. 23, 2015

(86) PCT No.: PCT/CN2015/092652
§ 371 (c)(1),
(2) Date: May 17, 2017

(87) PCT Pub. No.: WO2017/066987
PCT Pub. Date: Apr. 27, 2017

(65) Prior Publication Data
US 2018/0344323 A1 Dec. 6, 2018

(51) Int. Cl.
*A61B 17/122* (2006.01)
*A61B 17/128* (2006.01)
(Continued)

(52) U.S. Cl.
CPC ........ *A61B 17/122* (2013.01); *A61B 17/1227* (2013.01); *A61B 17/1285* (2013.01); *A61B 2017/00818* (2013.01); *A61B 2017/12004* (2013.01); *A61B 2090/034* (2016.02); *A61B 2090/037* (2016.02)

(58) Field of Classification Search
CPC .............. A61B 17/122; A61B 17/1227; A61B 17/1285; A61B 2017/00818; A61B 2017/12004; A61B 2090/034; A61B 2090/037
See application file for complete search history.

(56) References Cited

U.S. PATENT DOCUMENTS

2002/0128667 A1  9/2002  Kobayashi et al.
2002/0133178 A1  9/2002  Muramatsu et al.
(Continued)

FOREIGN PATENT DOCUMENTS

| CN | 102065780 A | 5/2011 |
|---|---|---|
| JP | 2002196909 A | 7/2002 |
| JP | 2004121485 A | 4/2004 |

OTHER PUBLICATIONS

International Search Report of PCT Patent Application No. PCT/CN2015/092652 dated Jan. 20, 2016.

*Primary Examiner* — Jocelin C Tanner (57) ABSTRACT

A ligation device comprises a clamp and a conveying unit. The clamp comprises a clip and a tightening tube to tighten a rear end of the clip therein, the clip comprises two clamping arms. The conveying unit comprises a traction line, a conveying tube and a control handle, the traction line runs through the conveying tube, the control handle is connected with a rear end of the conveying tube and a rear end of the traction line. At least one bearing piece is arranged at a tail of the clip and can be deformed or broken under a certain pressure, the bearing piece is assembled to form a hole, the traction line runs through the hole and a front end of the traction line is blocked by the bearing piece.

19 Claims, 12 Drawing Sheets

(51) Int. Cl.
*A61B 17/00* (2006.01)
*A61B 90/00* (2016.01)
*A61B 17/12* (2006.01)

(56) References Cited

U.S. PATENT DOCUMENTS

2005/0107809 A1\* 5/2005 Litscher ............... A61B 17/122
 606/142
2006/0271072 A1\* 11/2006 Hummel ............. A61B 17/122
 606/142

\* cited by examiner

LIGATION DEVICE

FIELD OF THE INVENTION

The present invention relates to the technical field of medical devices, and more particularly to a ligation device for treatment of active bleeding, wound and perforation closure.

BACKGROUND OF THE INVENTION

Stomach and intestine of an living body often bleed due to various diseases, accidents or damages caused by endoscopic treatment. As to active bleeding, it is usually treated by drug spraying, high-frequency electricity, laser, argon burning method of the bleeding site, or mechanical compression hemostasis method using hemostatic clamp. The mechanical compression hemostatic method using hemostatic clip is most reliable for treating non-variceal active bleeding, and is accepted by doctors and patients. As traditional clinical operation is more invasive, mucosa of the digestive tract is further damaged. Using clamp for closure of the mucosal wound of the digestive tract can spur healing, and also achieve effective closure of small perforation of the digestive tract, the effect of which is now accepted in clinical practice. This method can minimize the damage to the patient brought by laparotomy.

Japanese patents laid-open No. 2002-196909 and laid-open No. 2004-121485 disclose a clamping device for ligation of biological tissue, which comprises an insertion unit, a clamp unit, and a clamp operation unit. The insertion unit can be inserted into the endoscope channel which has been inserted into a body cavity of the living body; the clamping unit can be mounted on the top of the insertion unit detachably with respect to the top of the insertion unit, and includes a clamp; the clamp operation unit comprises an operation subunit which is exposed from the bottom of the insertion unit, a connection subunit which is not connected with the clamping unit and which cannot extend to the top of the insertion unit when operating from the outside, and a clamp which can use the operation subunit to open or close the clamping unit. The clamping unit has a connection structure, which can be operated by the clamp operation unit to move along the extending direction through the passage of the clamp. The connection structure has a break portion, which can be broken when the pulling force on the clamp operation unit is over a certain range. The connection structure is formed by injection molding a high-strength resin material such as liquid crystal polymer or nylon. One part of the outer peripheral surface of the break portion has a cut, which is formed in a radial direction and extends in a direction intersecting the moving direction of the clamp. Besides, the other ends of a plurality of elongate arms of the clamp which are connected to one another are locked in the cut.

In the patents above, the connection structure is made of polymer materials. Since the digestive tract is curved, the channel of the endoscope needs to be bended to reach the lesion location, especially in some special location, the channel of the endoscope needs to be bended to the limit to reach the lesion, thus the ligation device running through the channel of the endoscope also needs to be bended, which causes damage or strength degradation of the connection structure. This makes release of the clamp become difficult or even causes the clamping unit to fail and results in operation delay. Furthermore, the proximal end of the connection structure is connected with the clamp operation unit and is exposed to the outside of the holding structure, thus the clamping unit is too long to pass the channel of the endoscope, especially when the endoscope needs to be bended to a greater extent, it may be even harder for the ligation device to pass the channel of the endoscope to reach the lesion location for effective clamping. In this situation, the doctor needs to adjust the bending amplitude to make the clamping unit exposed to the outside of the channel of the endoscope. However, the lesion location will not be able to be observed by the endoscope for a period of time, which may cause risks, especially when the patient is bleeding heavily.

Therefore, a clamp device is in urgent need which can easily pass the channel of the endoscope to reach the lesion location and can be well released.

SUMMARY OF THE INVENTION

Considering the above, the purpose of the present invention is to provide a ligation device in which the clamp can pass the curved channel of the endoscope easily to reach the lesion location and simple and reliable clamp of the living tissues can be achieved.

In order to achieve the above purpose, the present invention provides a ligation device, comprising a clamp and a conveying unit, characterized in that the clamp comprises a clip and a tightening tube to tighten a rear end of the clip, the clip comprising two clamping arms;

the conveying unit comprises a traction line, a conveying tube and a control handle, wherein the traction line runs through the conveying tube, and the control handle is connected with a rear end of the conveying tube and a rear end of the traction line to drive the traction line to operate the clamp;

at least one bearing piece is arranged at a tail of the clip and can be deformed or broken under a certain pressure, the bearing piece is assembled to form a hole, the traction line runs through the hole and a front end of the traction line is blocked by the bearing piece, when the clamp is released, the bearing piece is deformed or broken under the force exerted by the front end of the traction line so that the clamp is disengaged from the conveying unit.

Preferably, each clamping arm has at least one bearing piece arranged at a tail, and bearing pieces of the two clamping arms are assembled to form the hole, which is unclosed.

Preferably, the bearing piece is arranged on only one of the clamping arms, and the bearing piece and a tail of the other one of the clamping arms are assembled to form the hole.

Preferably, tails of the two clamping arms are both bended to form two bending arms, the two bending arms being crossed so that the tails of the two clamping arms are connected, wherein each bending arm has one bearing piece arranged at a tail, bearing pieces of the two bending arms are assembled to form the hole, which is unclosed.

Preferably, one portion of the clip is symmetrically bended to form the two clamping arms, other portion of the clip which is not bended has one bearing piece provided at a tail, and the bearing piece and the portion of the clip which is symmetrically bended are assembled to form the hole.

Preferably, one of the clamping arms has an engagement piece, and the other one of the clamping arms has an engagement slot provided thereon, the engagement piece being inserted into the engagement slot to connect the tails of the two clamping arms.

Preferably, the tails of the two clamping arms are connected by a pin.

Preferably, a front end of the traction line comprises a front large-diameter section, a small-diameter section and a rear large-diameter section, the diameter of the front large-diameter section and the rear large-diameter section are larger than the diameter of the hole, the diameter of the small-diameter section is smaller that the hole, the small-diameter section is within the hole, and the front large-diameter section is stuck between the tails of the two clamping arms.

Preferably, a pulling head is provided at the front end of the traction line, the pulling head being stuck between the tails of the two clamping arms.

Preferably, the clamp comprises a stop tube which is connected with a rear end of the tightening tube, a stop stage is arranged at a front end of the tightening tube, and the bearing piece abuts against the stop stage.

Preferably, an accommodation tube is arranged outside of the conveying tube, the conveying tube running through the accommodation tube.

Preferably, a grip handle is mounted at a rear end of the accommodation tube, and a detachable stopper is arranged between the grip handle and the control handle.

Compared with the prior art, using the ligation device of the present invention can ensure more reliable release of the clamp and thus eliminate the risk caused by the performance reduction of the material of the connection structure that release of the clamp may be failed. Furthermore, in the present invention, the clamp and the traction line are connected within the tightening tube or the stop tube, which greatly shortens the length of the clamp and makes the ligation device more simplified and reliable. Thus it is easier for the ligation device to pass through the channel of the endoscope. The present invention provides a ligation device that is adapted to various parts in digestive tract, which greatly reduces the operation time and saves more time for the patients.

DETAILED DESCRIPTION OF ILLUSTRATED EMBODIMENTS

Preferred embodiments will be explained in the following detailed description taken in conjunction with the accompanying drawings. Apparently, the present invention is not limited to the embodiments herein.

The First Embodiment

Referring to FIG. 1, FIG. 2, FIG. 3 and FIG. 4, the ligation device comprises a clamp 1 and a conveying unit 2. The clamp 1 comprises a clip 11 and a tightening tube 12 to tighten the rear end of the clip 11, the clip 11 comprises clamping arms 111 and 112.

Figure 3:
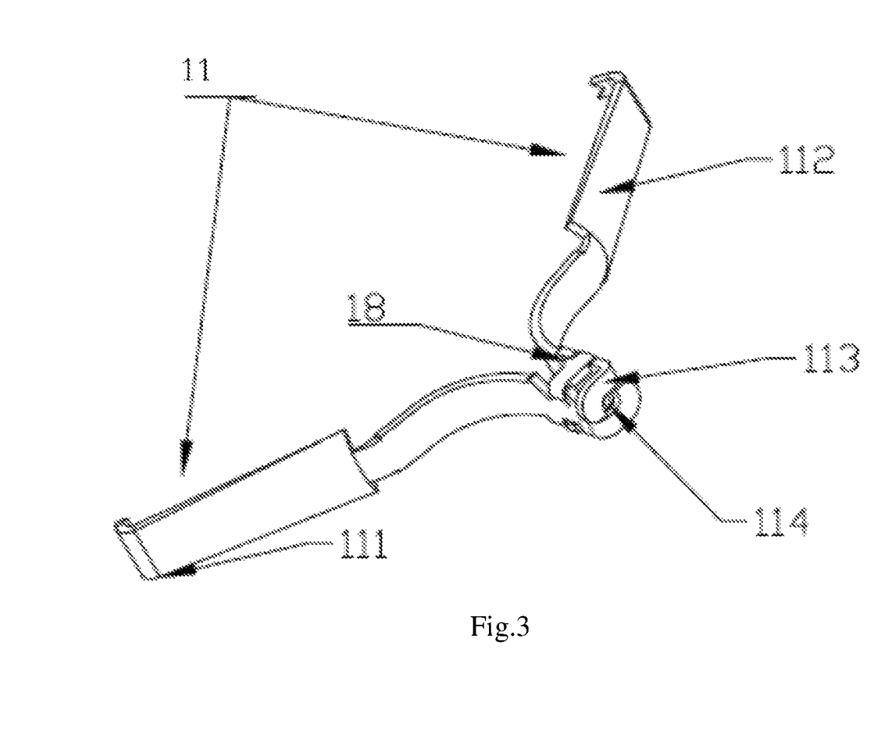
FIG. 3 is a schematic diagram of the clip according to the first embodiment of the present invention.
Figure 4:
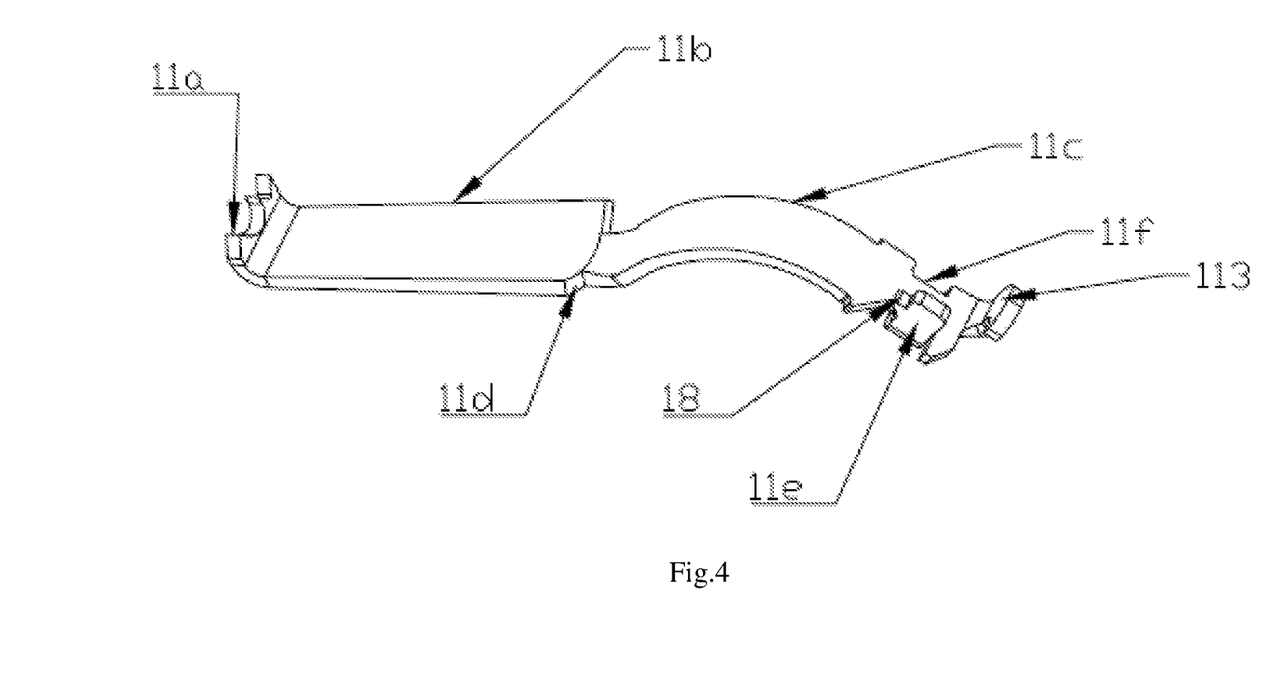
FIG. 4 is a schematic diagram of the clamping arm according to the first embodiment of the present invention.

The clamping arms are now described in detail with reference to FIG. 3 and FIG. 4. Each clamping arm has a front hook 11a provided at the front end, the rear end of the front hook 11a is connected with the main body 11b of the clamping arm, and the rear end of the main body 11b of the clamping arm is a bending arm 11c. The tails of the bending arms of the two clamping arms are connected together so that the two clamping arms can move synchronously, and a space is kept between the bending arms of the two clamping arms. The rear end of the main body 11b of the clamping arm has a stop stage 11d provided thereon. The rear ends of the bending arms for example are connected as follows: the rear end of the bending arm of the clamping arm 111 has an engagement piece 11e, the rear end of the bending arm of the clamping arm 112 has an engagement slot 11f, the engagement piece 11e is inserted into the engagement slot 11f so that the tails of the two bending arms are connected together; alternatively, the tails of the two bending arms can also have pin holes provided thereon and can be connected together by a pin. Moreover, each clamping arm can have a spacing stage 18 to abut against the bending arm of the other clamping arm, so that the bending arms of the two clamping arms are spaced apart at a certain distance.

Figure 1:
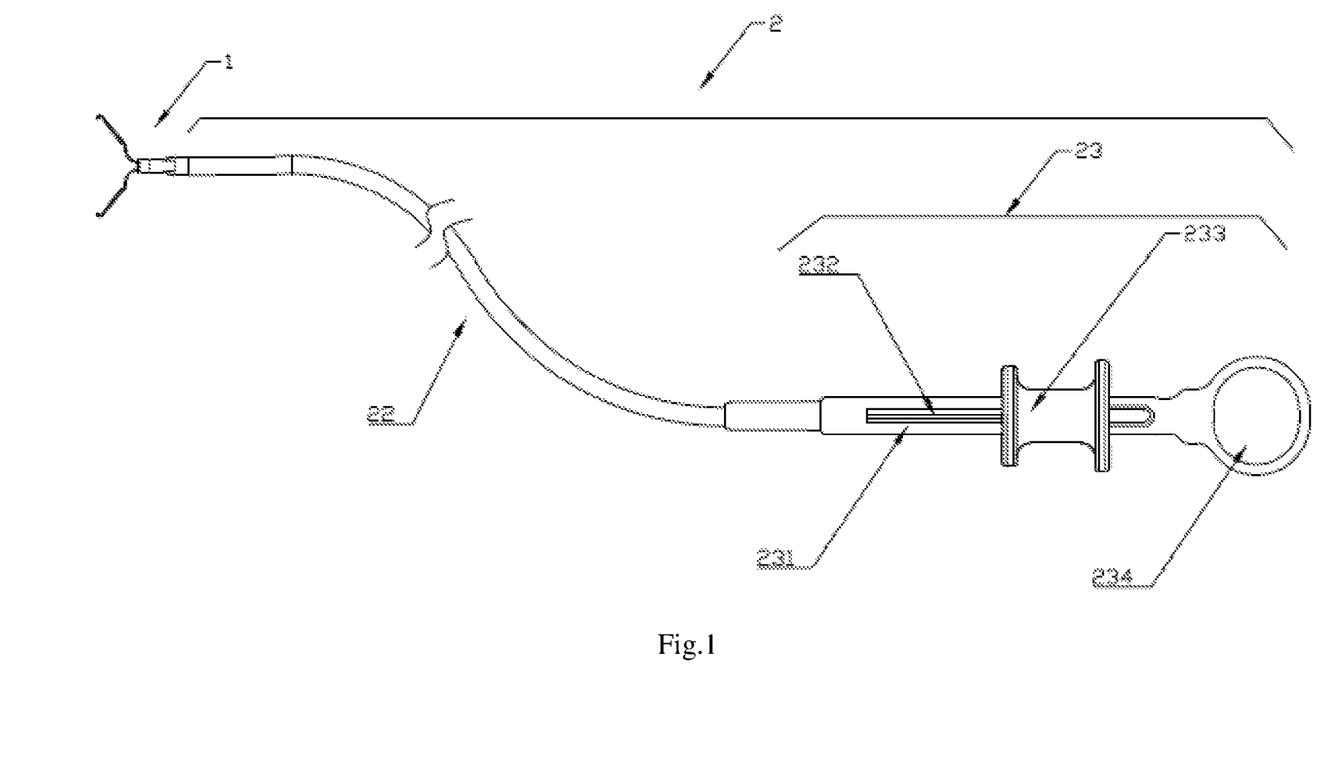
FIG. 1 is a schematic diagram of the ligation device of the present invention.
Figure 2:
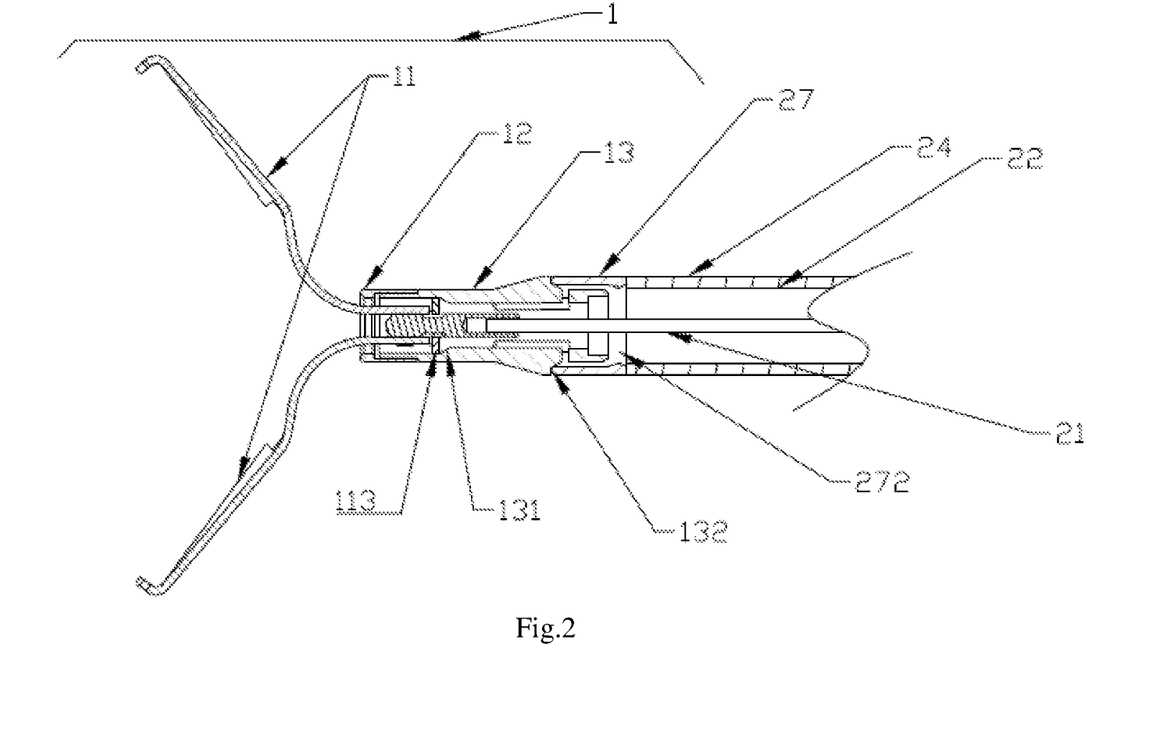
FIG. 2 is a schematic diagram showing assembly of the clip of the present invention.

Referring to FIG. 1 and FIG. 2, the conveying unit 2 comprises a traction line 21, a conveying tube 22 and a control handle 23. The traction line 21 runs through the conveying tube 22, the control handle 23 is connected with the rear end of the conveying tube 22 and the rear end of the traction line 21 to drive the traction line 21 to operate the clamp 1.

The clip 11 has at lease one bearing piece 113 arranged at its tail, which bearing piece can be deformed or broken under a certain pressure. The bearing piece 113 forms a hole 114 at the tail of the clip, the traction line 21 runs through the hole 114 and the front end of the traction line 21 is blocked by the bearing piece 113 so that the traction line is prevented from coming off from the hole. When the clamp 1 is released, the bearing piece 113 is deformed or broken under the force exerted by the front end of the traction line 21, so that the clamp 1 is disengaged from the conveying unit 2.

In the first embodiment, each clamping arm has a bearing piece 113, and the two bearing pieces form the hole 114 which is not unclosed.

Figure 5:
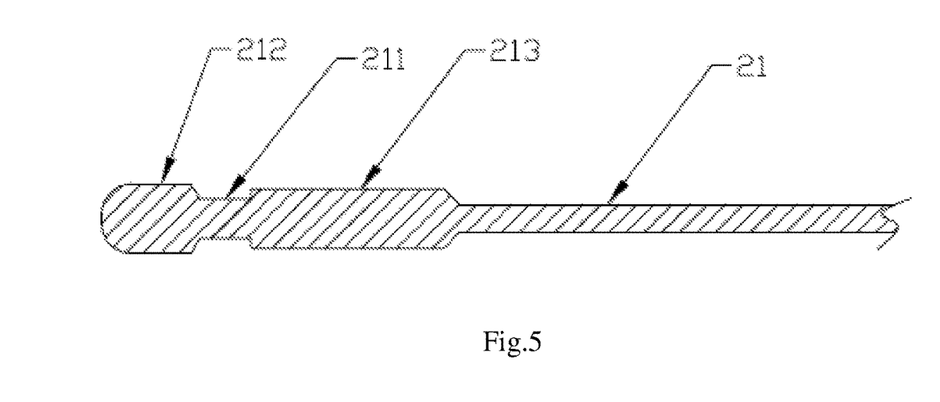
FIG. 5 is a schematic diagram of the traction line according to one embodiment of the present invention.

Further, as seen in FIG. 5, the head of the traction line 21 comprises from the front to the rear a front large-diameter section 212, a small-diameter section 211, and a rear large-diameter section 213. The effective diameters of the front large-diameter section 212 and the rear large-diameter section 213 are larger than the effective minimum diameter of the hole 114, the diameter of the small-diameter section 211 is smaller than the effective diameter of the hole 114. By having this design, the front large-diameter section 212 can run through the hole 114, and the front large-diameter section can be stuck between the tails of the two clamping arms, thus the clamp 1 and the conveying unit 2 are connected together. By providing this structure, the connection structure between the clamp 1 and the conveying unit 2 can be simplified, thus the length of the ligation device can be greatly reduced.

Figure 6:
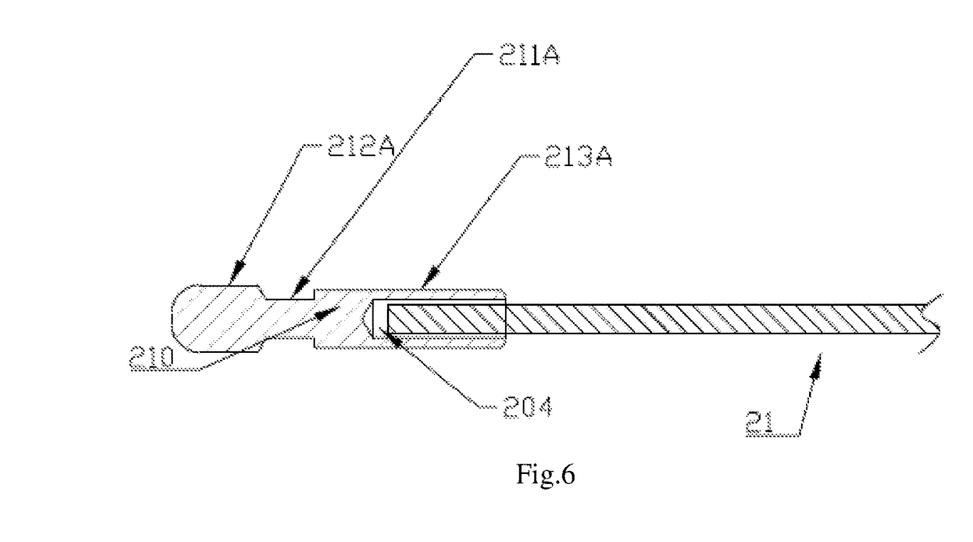
FIG. 6 is a schematic diagram of the traction line with a pulling head according to one embodiment of the present invention.

Preferably, as a variation of the first embodiment, as shown in FIG. 6, a pulling head 210 can be mounted in the front end of the traction line 21, and the pulling head 210 is stuck between the tails of the two clamping arms. Specifically, the pulling head 210 comprises a front large-diameter section 212A, a small-diameter section 211A, and a rear large-diameter section 213A. The diameter of the front large-diameter section 212A and the rear large-diameter section 213A are larger than the diameter of the hole 114, the diameter of the small-diameter section 211A is smaller than the diameter of the hole 114, the small-diameter section 211A can run through the hole 114, so the front large-diameter section 212A can be stuck between the tails of the two clamping arms, and thus the clamp 1 and the conveying unit 2 are connected together.

Figure 7:
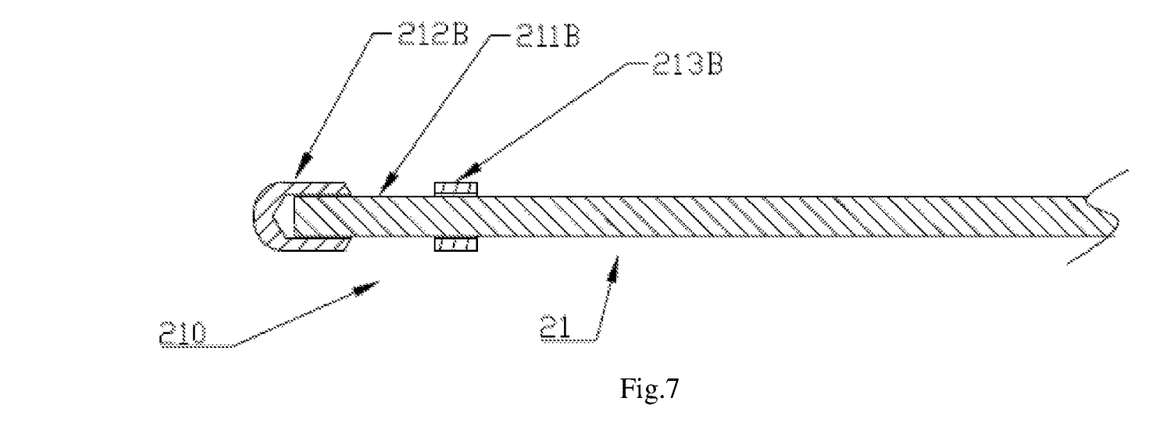
FIG. 7 is a schematic diagram of the traction line according to another embodiment of the present invention.

As shown in FIG. 7, in a preferred embodiment, a front large-diameter section 212B and a rear large-diameter section 213B are installed in the traction line 21, and a small-diameter section 211B is formed in the space between the front large-diameter section 212B and the rear large-diameter section 213B. The diameters of the front large-diameter section 212B and the rear large-diameter section 213B are larger than the diameter of the hole 114, and the diameter of the small-diameter section 211B is smaller than the diameter of the hole 114. The small-diameter section 211B can run through the hole 114, so the front large-diameter section 212B can be stuck between the tails of the two clamping arms and does not easily come out, and thus the clamp 1 and the conveying unit 2 are connected together.

Figure 8:
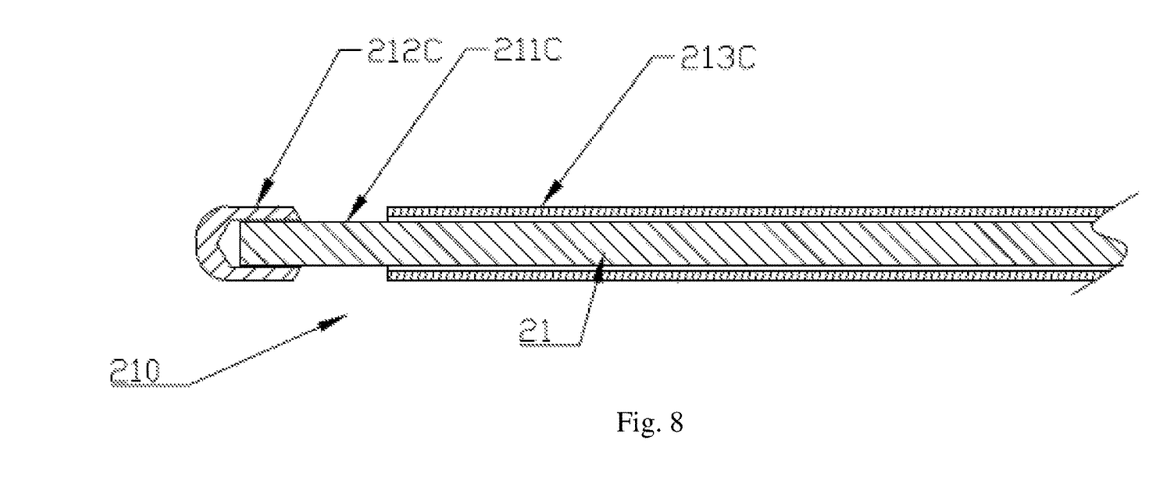
FIG. 8 is a schematic diagram of the traction line with a pulling head according to another embodiment of the present invention.

Preferably, as shown in FIG. 8, as a further variation of the pulling head, the pulling head can be an elongate tube which is formed by muf-coupling a front large-diameter section 212C and a rear large-diameter section 213C on the traction line 21. The front large-diameter section 212C and the rear large-diameter section 213C are movable with respect to the traction line 21. The maximum diameters of the front large-diameter section and the rear large-diameter section are larger than the effective diameter of the hole 114. A small-diameter section 211C is formed between the front large-diameter section 212C and the rear large-diameter section 213C.

It is to be noted that, the front large-diameter section can be driven by the traction line to pull the clip to effectively clamp the tissues. When the traction line is pulled backwards, the front large-diameter section moves backwards and breaks out from the bearing piece 113 and thus disengages from the hole 114, and thus the clamp 1 is disengaged from the conveying unit 2.

Figure 9:
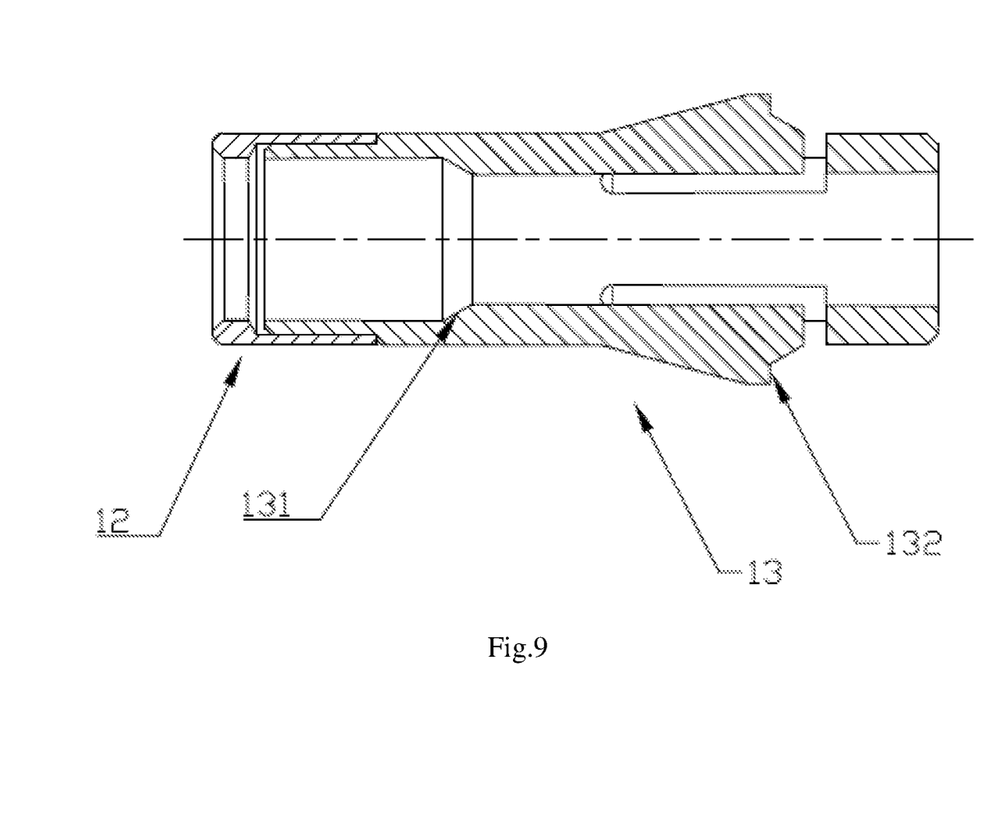
FIG. 9 is a section view of the stop tube of the present invention.

Further, the clamp 1 can comprise a stop tube 13. The stop tube 13 can be made of polymer materials, for example it can be made by injection molding by using PA (polyamide), nylon, liquid crystal polymer and PPA (Polyphthalamide), or it can be made by mechanically molding or powder metallurgy by using high elasticity metal materials. As shown in FIG. 2 and FIG. 9, the stop tube 13 is connected with the rear end of the tightening tube 12, and a stop stage 131 is provided at the front end of the stop tube 13. When the clamp 11 is pulled backwards to run through the tightening tube 12 and the inner hole of the stop tube 13, the bearing piece 113 abuts against the stop stage 131 of the stop tube, so that the clip 11 is prevented from further entering the stop tube 13. At the same time, the bearing piece 113 contacts with the inner wall of the stop tube 13, so that the clip 11 is prevented from coming off from the stop tube. An engagement portion 132 which can perform the function of elastic deformation is provided at the rear end of the stop tube 13. When the arms of the clip are drawn close under pressure, the engagement portion 132 is compressed elastically, and when the pressure is relieved, the engagement portion 132 restores to its expanded configuration. It is to be noted that, in the present invention, the tightening tube 12 can be inserted into the stop tube 13; or the tightening tube 12 and the stop tube 13 can be formed integrally without the engagement portion, and in this situation, the diameter of the tightening tube 12 is larger than the diameter of the conveying tube 22, and thus the tightening tube 12 can not be received by the conveying tube 22.

In the present invention, as shown in FIG. 2, an accommodation tube 24 with a flexible structure can be arranged outside of the conveying tube 22. The accommodation tube can receive the clips 1 therein, and the front end of the accommodation tube 24 is connected with a head tube 27.

Further, as shown in FIG. 1, the control handle 23 includes a handle body 231, an operation rod 232 running through the handle body 231, a slide handle 233 connected to the rear end of the operation rod 232 and an operation handle 234 fixed at the rear end of the handle body 231. The slide handle 233 is movably arranged on the handle body 231, the rear end of the conveying tube 22 is fixedly connected to the front end of the handle body 231, and the rear end of the traction line 21 is connected with the front end of the operation rod 232. The slide handle 233 can drive the operation rod 232 to move forwards and backwards to make the traction line 21 move along the conveying tube 22.

In the initial state, the clamp 1 is preassembled at the front end of the conveying unit 2, the clamp 1 is accommodated by the accommodation tube 24, the arms of the clip are folded, and the bearing piece 113 abuts against the stop stage 131 and contacts with the inner wall of the stop tube 13, and the engagement portion 132 of the stop tube is then compressed. In usage, the clamp 1 is conveyed by the conveying unit 2 through the channel of the endoscope and to the lesion of the digestive tract of the living body. Then the slide handle 233 is pushed forwards, so that the clamp 1 is pushed gradually out of the accommodation tube 24. The clips restore to its original expanded configuration, and at the same time, the engagement portion 132 restores to its original shape and prevents the clamp from inserting into the head tube 27. When the slide handle 233 is moved backwards, the clamp 1 will be driven to move backwards so that the engagement portion 132 abuts against the end face of the head tube 27, and the rear end of the stop tube 13 is inserted into the inner hole of the head tube 27. When the slide handle 233 is further pulled, the front end of the head tube will be blocked by the bearing piece of the clip 11. Then the clip 11 is pulled to move further backwards so that the clip is folded. When the stop stage 11d contacts with the front end of the tightening tube 12, the clip stops moving backwards. In this situation, continuing to exerted pulling force on the slide handle will cause the force on the bearing piece at the tail of the clamp 1 to increase drastically, and the bearing piece will be broken when the pulling force on the bearing piece is over a certain range. Then the front end of the traction line (the front large-diameter section 212/212A/212B/212C) will be disengaged from the hole 114, so that the clamp 1 is disengaged from the conveying unit 2 and stays in the digestive tract. The two clamping arms of the clip are fully folded and exerted enough pressure on the tissues of the living body to prevent blood flow of the tissues or to close the wound.

A Variation of the First Embodiment

Figure 10:
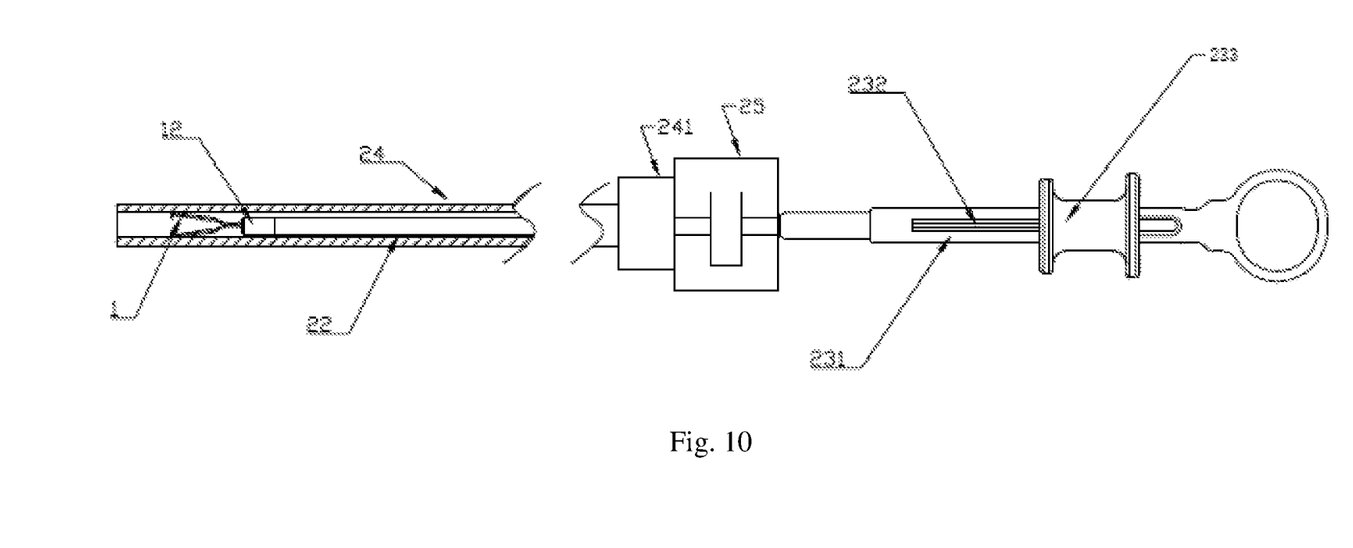
FIG. 10 is a schematic diagram of the ligation device according to a variation of the present invention.

As another implementation of the first embodiment, the conveying unit 2 is provided differently from the first embodiment. As shown in FIG. 10, the accommodation tube 24 extends to the front end of the handle body 231, and a grip handle 241 is arranged at the rear end of the accommodation tube 24. The holder 24 can drive the accommodation tube 24 to move along the conveying tube. A detachable stopper 25 can be mounted between the grip handle 241 and the handle body 231. When the stopper 25 is removed and the grip handle 241 moves backwards, the clamp 1 can be exposed. The clip 11 is expanded, and pulling the slide handle 233 causes the clamp to move towards the conveying tube. The tightening tube 12 is not able to move when it abuts against the conveying tube 22 (or when the stop tube abuts against the conveying tube in case that the tightening tube is connected with a stop tube). The slide handle 233 will continue to move backwards so that the traction line drives the clips to be folded to clamp the living tissues. When the clamping arms of the clip abut against the tightening tube 12, the clamp 1 cannot move anymore. In this situation, if pulling is continued, the bearing piece 113 will be deformed, which causes the front end of the traction line to be disengaged from the hole 114, so that the clamp 1 is disengaged from the conveying unit 2 and stays in the digestive tract.

The Second Embodiment

Figure 11:
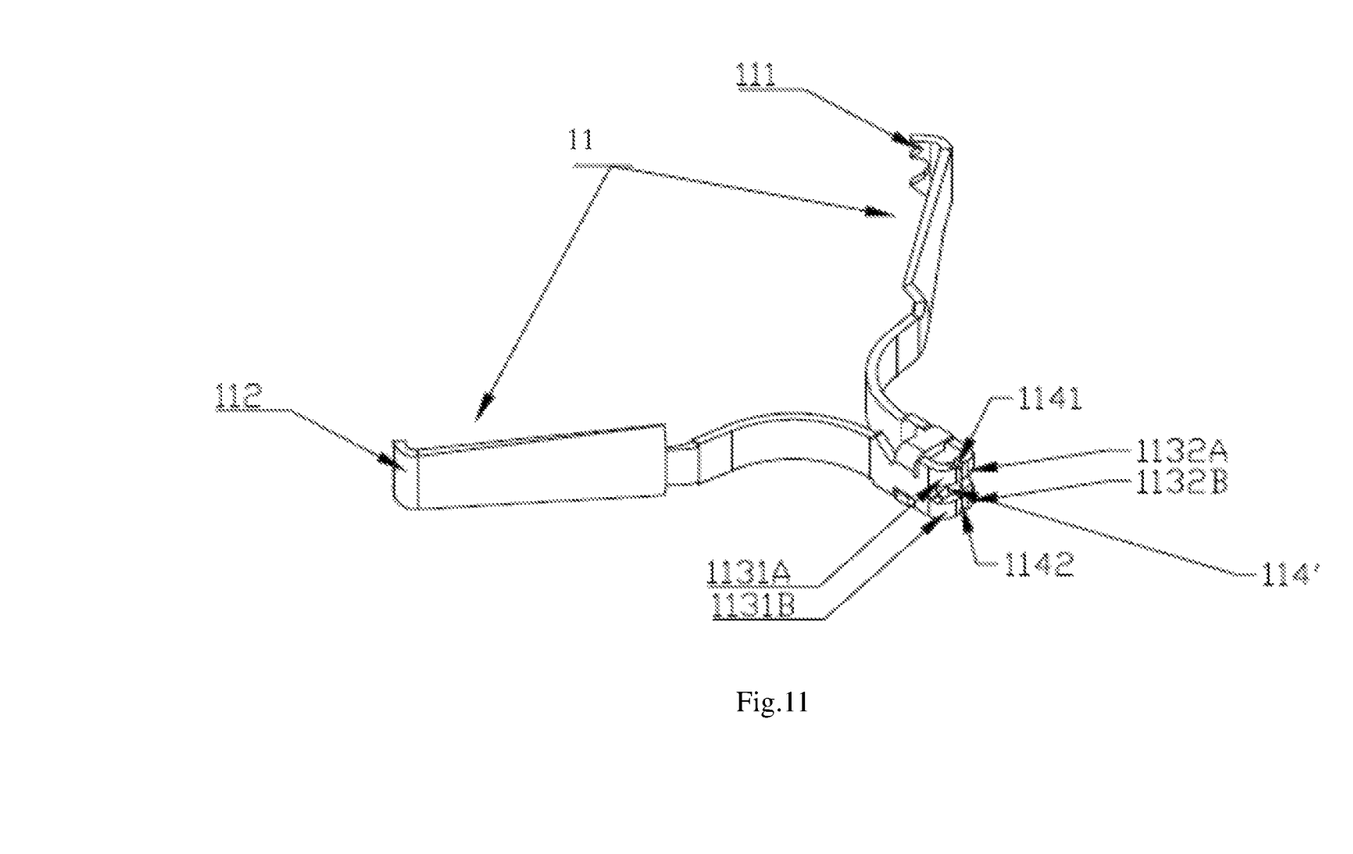
FIG. 11 is a schematic diagram of the clip according to the second embodiment of the present invention.

The difference between the second embodiment and the first embodiment lies in the structure of the clamping arm. As shown in FIG. 11, each clamping arm of the clip has at least one bearing piece (In this embodiment, each clamping arm has two bearing pieces). The rear end of the clamping arm 111 has bearing pieces 1132A and 1132B, and the rear end of the clamping arm 112 has bearing pieces 1131A and 1131B. An unclosed groove 1141 is formed between the bearing pieces 1131A and 1132A, and an unclosed groove 1142 is formed between the bearing pieces 1131B and 1132B. An unclosed hole 114' is formed by these four bearing pieces 1131A, 1132A, 1131B and 1132B.

As shown in FIG. 11, the rear ends of the two clamping arms are connected together by an engagement piece and an engagement slot. Alternatively, the rear ends of the two clamping arms are provided with pin holes and can be connected together by a pin. It is to be noted that, the rear ends of the two clamping arms can be connected by any method that achieves synchronous movement of the two clamping arms.

In the second embodiment, like in the first embodiment, the front end of the traction line or the pulling head arranged at the front end of the traction line comprises a front large-diameter section, a rear large-diameter section, and a small-diameter section between the front large-diameter section and the rear large-diameter section. The small-diameter section is stuck in the hole 114' and cannot come out easily, so that the clamp 1 and the conveying unit 2 are connected together. By providing this structure, the connection structure between the clamp 1 and the conveying unit can be simplified, and thus the length of the ligation device can be greatly reduced.

It is to be noted that, the ligation device of the present invention can also be embodied by combination of any variation of the clip of the second embodiment and any variation of the conveying unit of the first embodiment.

The Third Embodiment

Figure 12:
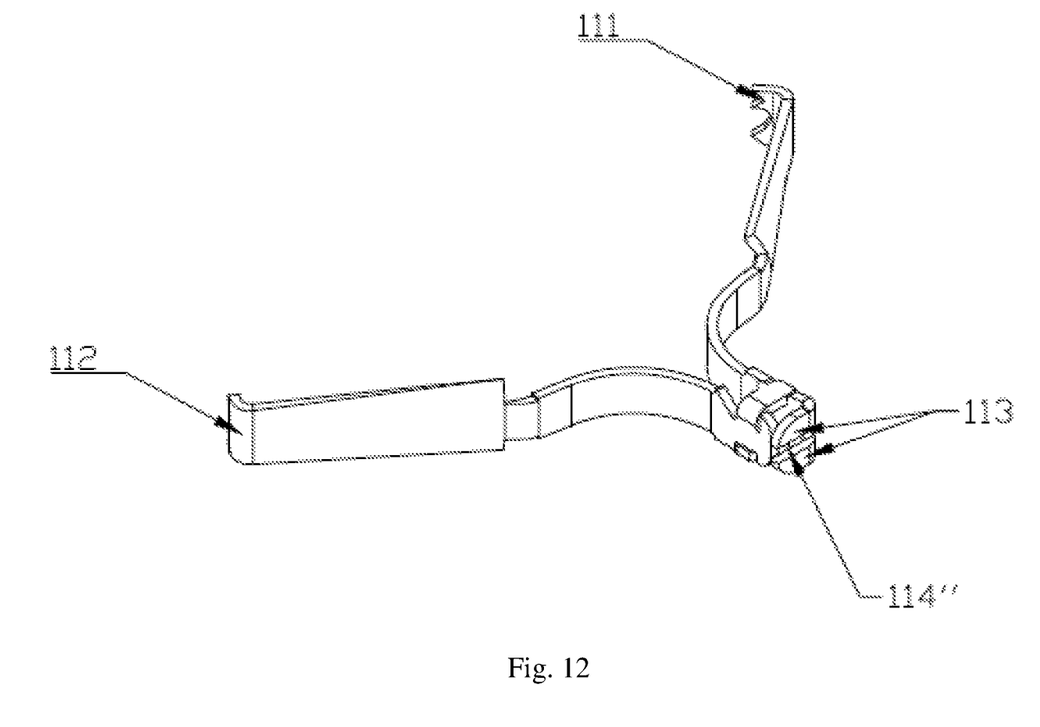
FIG. 12 is a schematic diagram of the clip according to the third embodiment of the present invention.

The difference between the third embodiment and the first embodiment lies in the structure of the clamping arms. As shown in FIG. 12, two bearing pieces 113 are only arranged on the clamping arm 111, the two bearing pieces 113 and the tail of the clamping arm 112 are assembled to form an unclosed hole 114".

As shown in FIG. 12, the tails of the two clamping arms are connected together by an engagement piece and an engagement slot. Alternatively, the tails of the two clamping arms are provided with pin holes and can be connected together by a pin. It is to be noted that, the tails of the two clamping arms can be connected by any method that achieves synchronous movement of the two clamping arms.

In the third embodiment, like in the first embodiment, the front end of the traction line or the pulling head arranged at the front end of the traction line comprises a front large-diameter section, a rear large-diameter section, and a small-diameter section between the front large-diameter section and the rear large-diameter section. The small-diameter section is stuck in the hole 114" and cannot come out easily, so that the clamp 1 and the conveying unit 2 are connected together. By providing this structure, the connection structure between the clamp 1 and the conveying unit can be simplified, and thus the length of the ligation device can be greatly reduced.

It is to be noted that, the ligation device of the present invention can also be embodied by combination of any variation of the clip of the third embodiment and any variation of the conveying unit of the first embodiment.

The Forth Embodiment

Figure 13:
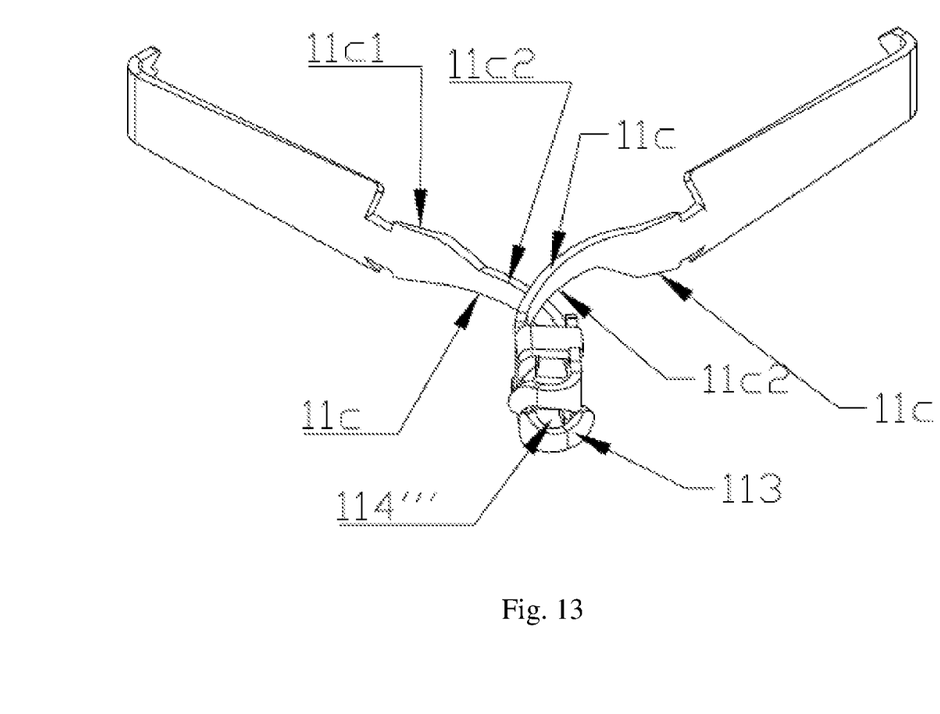
FIG. 13 is a schematic diagram of the clip according to the forth embodiment of the present invention.

The difference between the forth embodiment and the first embodiment lies in the structure of the clamping arms. As shown in FIG. 13, the bending arms 11c at the tails of the clamping arms form a crossover structure so that the tails of the clamping arms are connected together. Each bending arm 11c has an eccentric arm 11c2, and the two sidelines of the eccentric arms run oppositely with respect to the central axis of the clip, so that the two bending arms are crossed without hindering each other's movement. A bearing piece 113 is provided at the tail of each bending arm, and the bearing pieces are assembled to form an unclosed hole 114'''. A bending portion 11c1 is provided for each bending arm, and the sidelines of the two bending portions cross the central axis of the clip. When the two clamping arms are folded, the two bending portions abut against each other and fold up in the tightening tube 12. Elastic force is generated so that the clip and the tightening tube are held closer to each other, and thus the clamping arms can be folded tightly. By providing eccentric arms, the clamping arms have a wider clamping angle and can be expanded to clamp more living tissues.

Likewise, in the forth embodiment, the bearing pieces of the clip forms a hole 114''', and the front end of the traction line or the pulling head arranged at the front end of the traction line comprises a front large-diameter section, a rear large-diameter section, and a small-diameter section between the front large-diameter section and the rear large-diameter section. The small-diameter section is stuck in the hole 114''' and cannot come out easily, so that the clamp 1 and the conveying unit 2 are connected together. By providing this structure, the connection structure between the clamp 1 and the conveying unit can be simplified, and thus the length of the ligation device can be greatly reduced.

It is to be noted that, the ligation device of the present invention can also be embodied by combination of any variation of the clip of the forth embodiment and any variation of the conveying unit of the first embodiment.

The Fifth Embodiment

Figure 14:
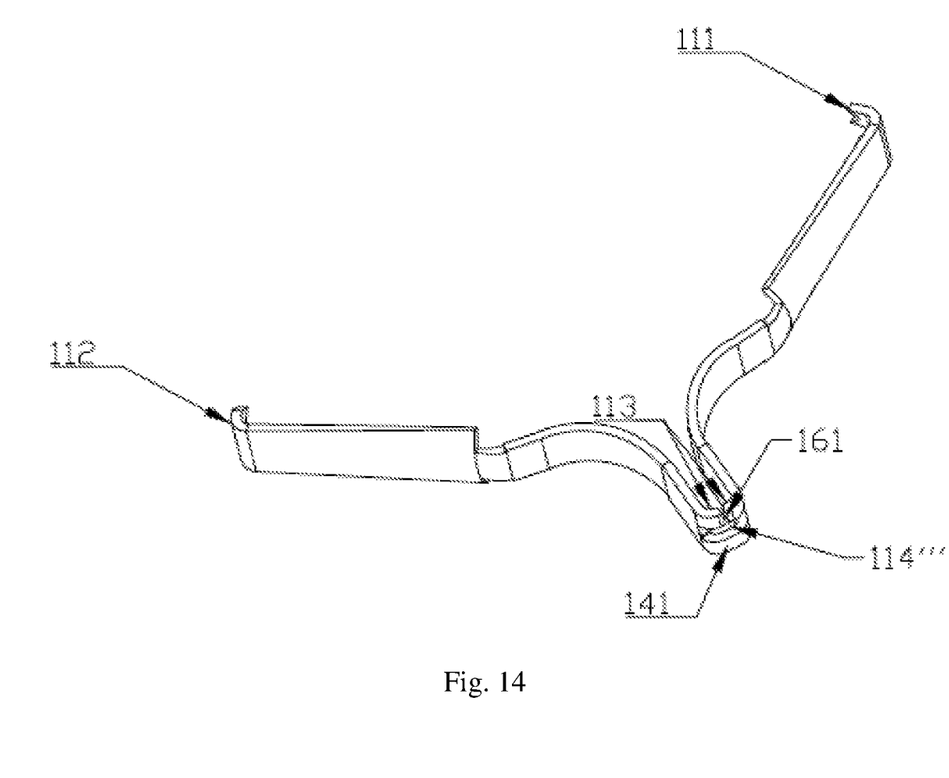
FIG. 14 is a schematic diagram of the clip according to the fifth embodiment of the present invention.

The difference between the fifth embodiment and the first embodiment lies in the structure of the clamping arms. As shown in FIG. 14, one portion of the clip is symmetrically bended to form two clamping arms so that the second halves of the tails of the two clamping arms are integrated. The first half of the tail of each clamping arm has a bearing piece 113 provided thereon, a slot 161 is formed between the two bearing pieces, and the bearing pieces and the tail of the clamping arm are assembled to form a hole 114'''' in the bending portion 141.

Likewise, in the forth embodiment, the bearing pieces of the clip forms a hole 114'''', and the front end of the traction line or the pulling head arranged at the front end of the traction line comprises a front large-diameter section, a rear large-diameter section, and a small-diameter section between the front large-diameter section and the rear large-diameter section. The small-diameter section is stuck in the hole 114'''' and does not come out easily, so that the clamp 1 and the conveying unit 2 are connected together. By providing this structure, the connection structure between the clamp 1 and the conveying unit can be simplified, and thus the length of the ligation device can be greatly reduced.

It is to be noted that, the ligation device of the present invention can also be embodied by combination of any variation of the clip of the fifth embodiment and any variation of the conveying unit of the first embodiment.

Instead of traditional connection-release structure, the present invention uses a bearing piece which can be broken or deformed under pressure, so as to ensure more reliable release of the clamp and thus eliminate the risk caused by the performance reduction of the material of the connection structure that release of the clamp may be failed. Furthermore, in the present invention, the clamp and the traction line are connected within the tightening tube or the stop tube, which greatly shortens the length of the clamp and makes the ligation device more simplified and reliable. Thus it is easier for the ligation device to pass through the channel of the endoscope. The present invention provides a ligation device that is adapted to various parts in digestive tract, which greatly reduces the operation time and saves more time for the patients.

While the invention has been described in connection with what are presently considered to be the most practical and preferred embodiments, it is to be understood that the invention is not limited to the disclosed embodiments, but on the contrary, is intended to cover various modifications and equivalent arrangements included within the spirit and scope of the invention.

What is claimed is:

1. A ligation device, comprising a clamp and a conveying unit, characterized in that
the clamp comprises a clip and a tightening tube to tighten a rear end of the clip therein, the clip comprising two clamping arms;
the conveying unit comprises a traction line, a conveying tube and a control handle, the traction line running through the conveying tube;
wherein at least one bearing piece is arranged at a tail of the clip and can be deformed or broken under a certain pressure, the at least one bearing piece is assembled to form a hole, the traction line runs through the hole and a front end of the traction line is blocked by the at least one bearing piece, when the clamp is released, the at least one bearing piece is deformed or broken under force exerted by the front end of the traction line so that the clamp is disengaged from the conveying unit;
the front end of the traction line comprises a front large-diameter section, a small-diameter section and a rear large-diameter section, the diameter of the front large-diameter section and the rear large-diameter section are larger than the diameter of the hole, the diameter of the small-diameter section is smaller than the hole, the small-diameter section is within the hole, and the front large-diameter section is stuck between tails of the two clamping arms.

2. The ligation device according to claim 1, characterized in that each clamping arm has the at least one bearing piece arranged at the tail of the clamping arm, the bearing pieces of the two clamping arms are assembled to form the hole, which is unclosed.

3. The ligation device according to claim 2, characterized in that one of the clamping arms has an engagement piece, and the other one of the clamping arms has an engagement slot provided thereon, the engagement piece being inserted into the engagement slot to connect the tails of the two clamping arms.

4. The ligation device according to claim 2, characterized in that the tails of the two clamping arms are connected by a pin.

5. The ligation device according to claim 2, characterized in that a front end of the traction line comprises a front large-diameter section, a small-diameter section and a rear large-diameter section, the diameter of the front large-diameter section and the rear large-diameter section are larger than the diameter of the hole, the diameter of the small-diameter section is smaller that the hole, the small-diameter section is within the hole, and the front large-diameter section is stuck between the tails of the two clamping arms.

6. The ligation device according to claim 2, characterized in that a pulling head is provided at the front end of the traction line, the pulling head being stuck between the tails of the two clamping arms.

7. The ligation device according to claim 2, characterized in that the clamp comprises a stop tube which is connected with a rear end of the tightening tube, a stop stage is arranged at a front end of the tightening tube, and the bearing piece abuts against the stop stage.

8. The ligation device according to claim 1, characterized in that the at least one bearing piece is arranged on the tail of only one of the clamping arms, and the bearing piece and a tail of the other one of the clamping arms are assembled to form the hole.

9. The ligation device according to claim 8, characterized in that one of the clamping arms has an engagement piece, and the other one of the clamping arms has an engagement slot provided thereon, the engagement piece being inserted into the engagement slot to connect the tails of the two clamping arms.

10. The ligation device according to claim 8, characterized in that a front end of the traction line comprises a front large-diameter section, a small-diameter section and a rear large-diameter section, the diameter of the front large-diameter section and the rear large-diameter section are larger than the diameter of the hole, the diameter of the small-diameter section is smaller that the hole, the small-diameter section is within the hole, and the front large-diameter section is stuck between the tails of the two clamping arms.

11. The ligation device according to claim 8, characterized in that a pulling head is provided at the front end of the traction line, the pulling head being stuck between the tails of the two clamping arms.

12. The ligation device according to claim 1, characterized in that each of the two clamping arms has a bending arms, the two bending arms being crossed so that the tails of the two clamping arms are connected, wherein each bending arm has one bearing piece arranged at a tail of the bending arm, the bearing pieces of the two bending arms are assembled to form the hole, which is unclosed.

13. The ligation device according to claim 12, characterized in that a front end of the traction line comprises a front large-diameter section, a small-diameter section and a rear large-diameter section, the diameter of the front large-diameter section and the rear large-diameter section are larger than the diameter of the hole, the diameter of the small-diameter section is smaller that the hole, the small-diameter section is within the hole, and the front large-diameter section is stuck between the tails of the two clamping arms.

14. The ligation device according to claim 1, characterized in that one portion of the clip is symmetrically bended to form the two clamping arms and a bending portion between the two clamping arms, one half of the tail of each clamping arm has one bearing piece provided thereon, and the bearing pieces and the tails of the clamping arms in the bending portion are assembled to form the hole.

15. The ligation device according to claim 14, characterized in that a front end of the traction line comprises a front large-diameter section, a small-diameter section and a rear large-diameter section, the diameter of the front large-diameter section and the rear large-diameter section are larger than the diameter of the hole, the diameter of the small-diameter section is smaller that the hole, the small-diameter section is within the hole, and the front large-diameter section is stuck between the tails of the two clamping arms.

16. The ligation device according to claim 1, characterized in that the clamp comprises a stop tube which is connected with a rear end of the tightening tube, a stop stage is arranged at a front end of the tightening tube, and the bearing piece abuts against the stop stage.

17. The ligation device according to claim 1, characterized in that an accommodation tube is arranged outside of the conveying tube, the conveying tube running through the accommodation tube.

18. The ligation device according to claim 17, characterized in that a grip handle is mounted at a rear end of the accommodation tube, a detachable stopper is arranged between the grip handle and the control handle.

19. A ligation device, comprising a clamp and a conveying unit, characterized in that the clamp comprises a clip and a tightening tube to tighten a rear end of the clip therein, the clip comprising two clamping arms; the conveying unit comprises a traction line, a conveying tube and a control handle, the traction line running through the conveying tube;
wherein at least one bearing piece is arranged at a tail of the clip and can be deformed or broken under a certain pressure, the at least one bearing piece is assembled to form a hole, the traction line runs through the hole and a front end of the traction line is blocked by the at least one bearing piece, when the clamp is released, the at least one bearing piece is deformed or broken under force exerted by the front end of the traction line so that the clamp is disengaged from the conveying unit;
a pulling head is provided at the front end of the traction line, and the pulling head is stuck between tails of the two clamping arms; the pulling head comprises a front large-diameter section, a small-diameter section and a rear large-diameter section, the diameter of the front large-diameter section and the rear large-diameter section are larger than the diameter of the hole, the diameter of the small-diameter section is smaller than the hole, the small-diameter section is within the hole.

\* \* \* \* \*